US009022946B2

(12) United States Patent
Haque

(10) Patent No.: US 9,022,946 B2
(45) Date of Patent: May 5, 2015

(54) CONTAMINATION REMOVAL FROM SENSORS PLACED IN AN AIRWAY

(75) Inventor: Kamran Haque, Riverside, CA (US)

(73) Assignee: CareFusion 207, Inc., San Diego, CA (US)

(*) Notice: Subject to any disclaimer, the term of this patent is extended or adjusted under 35 U.S.C. 154(b) by 881 days.

(21) Appl. No.: 12/783,867

(22) Filed: May 20, 2010

(65) Prior Publication Data

US 2011/0288429 A1 Nov. 24, 2011

(51) Int. Cl.
*A61B 5/08* (2006.01)
*A61M 16/00* (2006.01)
*A61M 16/08* (2006.01)
*A61M 16/16* (2006.01)

(52) U.S. Cl.
CPC ............... *A61M 16/00* (2013.01); *A61B 5/082* (2013.01); *A61M 16/16* (2013.01); *A61M 2205/10* (2013.01); *A61M 2205/11* (2013.01); *A61M 2209/10* (2013.01); *A61M 16/0833* (2013.01)

(58) Field of Classification Search
None
See application file for complete search history.

(56) References Cited

U.S. PATENT DOCUMENTS

| 6,039,696 | A * | 3/2000 | Bell .............................. 600/532 |
| 7,263,994 | B2 | 9/2007 | Gradon et al. |
| 2002/0028999 | A1* | 3/2002 | Schaldach et al. ............ 600/486 |
| 2004/0007387 | A1* | 1/2004 | Bar-Cohen et al. ............. 175/50 |
| 2005/0280712 | A1* | 12/2005 | Kawai ...................... 348/207.99 |
| 2007/0215154 | A1 | 9/2007 | Borrello |
| 2008/0135044 | A1 | 6/2008 | Freitag et al. |
| 2008/0283062 | A1 | 11/2008 | Esposito, Jr. |
| 2009/0156953 | A1 | 6/2009 | Wondka et al. |

OTHER PUBLICATIONS

PCT Search Report and Written Opinion mailed Feb. 9, 2012, 10 pgs.
International Preliminary Report on Patentability for PCT/US2011/036785, International Filing Date of May 17, 2011.

* cited by examiner

*Primary Examiner* — Patricia Mallari
*Assistant Examiner* — Michael J Burrage
(74) *Attorney, Agent, or Firm* — McDermott Will & Emery LLP

(57) ABSTRACT

A sensor assembly includes a sensing element and an actuator. The sensing element measures a parameter associated with gas in an airway. The actuator actuates the sensing element to prevent contamination build up on the sensing element.

28 Claims, 1 Drawing Sheet

CONTAMINATION REMOVAL FROM SENSORS PLACED IN AN AIRWAY

BACKGROUND

Respiratory therapy systems are designed to assist a patient who has difficulty breathing or is unable to breath. In general terms, respiratory therapy systems include a ventilator, an optional humidifier including a heater plate, and a patient circuit. When a humidifier is used, the ventilator supplies gases to a humidification chamber coupled with the humidifier. Water within the humidification chamber is heated by the humidifier heater plate, which produces water vapor that humidifies gases passing through the chamber. From the chamber, humidified gases are then delivered to the patient through the breathing circuit. One or more breathing tubes of the patient circuit may be heated to maintain a desired temperature of gas (as used herein, the term "gas" can comprise a single type of gas (e.g., oxygen) or a mixture of multiple types of gases (e.g., a mixture of helium and oxygen) within the one or more breathing tubes.

Current respiratory therapy systems (either with or without a humidifier), utilize one or more sensors to measure various parameters associated with gas in the systems. Quantitative measurement of parameters acquired from one or more sensors are used to control the systems output to a desirable set point. Example parameters may include relative humidity, temperature, flow, pressure, etc. The one or more sensors are positioned within an airway of the patient circuit and are integrated with a sensing element to measure parameters. During the coarse of delivering the humidified gases, within the airway of the breathing tubes, the integrated sensing element of the sensor(s) can be subjected to contamination due to introduction of various particles (e.g., water, salt, aerosolized medicine). The accumulation of contamination on the sensing element over time can cause incorrect measurements, ultimately resulting in improper operation and/or failure of the respiratory therapy system. For example, a safety critical feedback sensor, once subjected to contamination, can produce a signal that is drastically higher or lower in relation to a controlled system output set point, resulting in potentially unsafe output of the system (e.g., incorrect medication dosage, elevated temperature, lower temperature, etc.).

In general, contamination accumulation may occur from residual water and particulates that forms a film on the sensor/sensing element surface for the inter and/or intra respiratory therapy session. For example, residual water on the sensor, after a therapy session, dries off, leaving a film of water marks, salt residue, etc. on a sensor surface. This film can impede the sensing capability of the sensor. For example, a capacitive membrane sensor absorbs and releases water relative to an environmental humidity. The change in capacitance produces electrical signals proportional to a calibrated voltage (or current) threshold. The accumulation of residual contamination can shift the signal threshold and could result in erroneous and/or erratic operation of a control system output.

When using an integrated relative humidity/temperature sensor, failure of the sensor can be especially prevalent when exposed to residual contamination accumulated over time, either intra-therapy (during use) or post therapy session (after use or many uses). In particular, residual contamination can cause output of a sensing element to shift (or fail) from calibrated values resulting in dangerously high outputs, which can compromise patient safety. For example, contamination on a surface of the sensor (e.g., a capacitive or resistive membrane) can result in incorrect delivery of elevated gas temperatures for an extended period of time to the patient. This situation can be undesirable and potentially cause damage to epidermal cells of the patient.

SUMMARY

Aspects of the present disclosure relate to a sensor assembly for positioning in an airway of a patient circuit to measure at least one parameter associated with gas (e.g., comprised of a single gas or a mixture of multiple gases) in the airway. The sensor assembly includes a sensing element mechanically coupled to an actuator. During use, the actuator actuates the sensing element. In one aspect, the sensor assembly is part of a respiratory therapy system, including the sensing element and actuator. The sensor assembly is positioned within an airway of the respiratory therapy system to measure a parameter. In yet another aspect, a method for improving reliability, repeatability and accuracy of dosage during a respiratory therapy session to a patient is disclosed. The method includes positioning a sensor assembly within an airway and actuating the sensor assembly.

DETAILED DESCRIPTION

Figure 1:
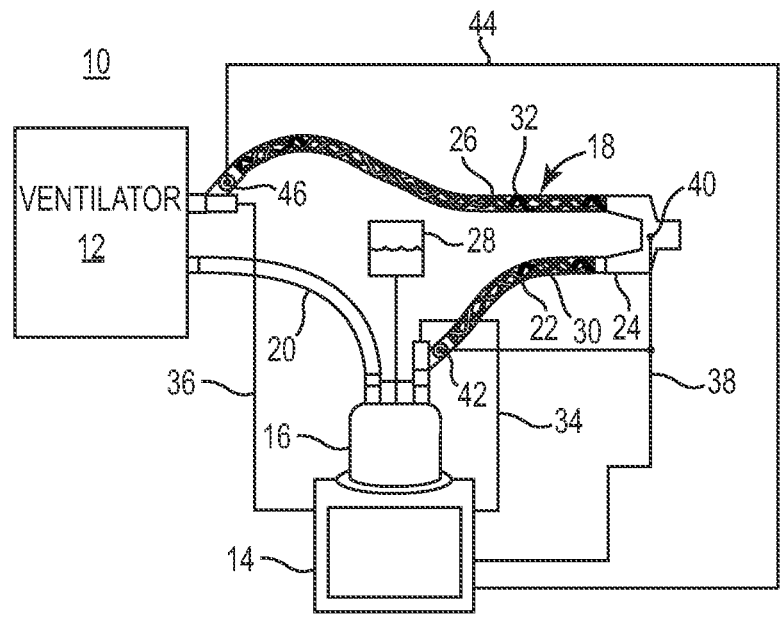
FIG. 1 is a schematic view of a respiratory humidification system employing a sensor assembly.

FIG. 1 is a schematic view of a respiratory humidification system 10 including a ventilator 12, humidifier 14 having a humidification chamber 16 and a patient circuit 18. It is worth noting that system 10 is one exemplary environment for concepts presented herein. For example, other forms of respiratory therapy can be used with concepts presented herein such as a CPAP (Continuous Positive Airway Pressure) system, invasive system, non-invasive system or other system that may add or remove one or more of the components of system 10.

In the embodiment illustrated, ventilator 12 supplies gases to humidification chamber 16 through an initial tube 20. Humidifier 14 heats water within the chamber 16 which is then output to patient circuit 18. Patient circuit 18 includes an inspiratory breathing tube (or limb) 22, a Y-connector 24 and an expiratory breathing tube (or limb) 26. In alternative embodiments, for example in a CPAP system, the Y-connector 24 and/or expiratory conduit 26 can be eliminated. In other embodiments, humidification chamber 16 can be eliminated. During use, inspiratory tube 22 transmits humidified gases from chamber 16 to a patient through a Y-connector 24. The Y-connector 24 can be selectively coupled to a patient interface such as an endotracheal tube. Other patient interfaces can include masks, nasal prongs, etc. After breathing in the humidified gases, the patient can exhale, transmitting exhaled gases through expiratory tube 26 back to ventilator 12. Liquid solution is supplied to the chamber 16 from a source 28, which, in one embodiment comprises a bag of liquid solution (e.g., water) coupled to chamber 16.

Inspiratory tube 22 and expiratory tube 26 include heating elements (e.g. wires) 30 and 32, respectively, positioned therein that, when heated, maintains a temperature of gas in the inspiratory tube 22 and/or expiratory tube 26. Humidifier 14 supplies electrical power to elements 30 and 32 through electrical connectors 34 and 36, respectively. Elements 30 and 32 are generally helically shaped and selected with a desired resistance in order to heat humidified gas within tubes 22 and 26, respectively, to a desired level.

Additionally, humidifier 14 receives electrical signals from a sensor input connector 38, interfaced with sensor assemblies 40 and 42. Sensor assembly 40 is positioned within Y-connector 24 (and proximate the patient) whereas sensor assembly 42 is positioned within inspiratory tube 22 (and proximate humidification chamber 16). If desired, a second sensor input connector 44 can provide further electrical signals to humidifier 14. Connector 44 is coupled to a sensor assembly 46 positioned within expiratory tube 26, proximate ventilator 12. Other sensor assemblies in various positions can further be provided. Sensor assemblies 40, 42, and 46 provide one or more measurements to humidifier 14, such as, temperature, relative humidity and/or flow information of gases within the patient circuit 18. Humidifier 14 uses this information to control power provided to elements 30 and 32 as well as control the temperature of fluid within chamber 16. In one example, sensor assemblies 40, 42, and 46 are identical and measure relative humidity and temperature in order to provide feedback to humidifier 14 indicative of relative humidity and temperature within system 10. In a further embodiment, information from sensor assemblies 40, 42 and 46 can also be provided to ventilator 12 for controlling the output of the system 10.

Sensor assemblies 40, 42, and 46 are sterilized before each use and may be single use (i.e., disposable) or multi-use. In the case of reusable sensor assemblies, it is desirable to utilize reliable and efficient cleaning approaches to maintain safe and sterilized components so as to prevent contamination of patient circuit 18. In some examples, autoclaving (which includes high temperature sterilization with pressurized steam cleaning) is one method commonly used to sterilize sensor assemblies 40, 42, and 46. However, some components within the assemblies 40, 42, and 46 can not be sterilized using autoclaves as the process can damage components. Thus, other reliable cleaning methods are employed in particular situations.

Independent of utilizing a single use or multiple use sensor assembly, relative humidity and temperature sensing integrated within the patient circuit 18 and in particular proximate Y-connector 24 can be beneficial to patient safety and for precise control of humidifier 14. For example, hazard conditions such as thermal overshoots, over the limits enthalpy, energy vapor dosage over extended periods, dry chamber protection, no flow due to blockage or to excessive rainout can be monitored and controlled in a timely fashion. The percentage relative humidity information to the humidifier 14 also serves a critical feedback path for humidification dosage optimization in various therapy modes such as manual and standard modes. Other benefits include data logging of percent relative humidity vs. temperature over time, thermal overshoot tracking and direct real time polling of miscellaneous measurements within the close proximity to the patient.

As provided below, the sensor assemblies 40, 42, and 46 of system 10 apply high frequency oscillations to a sensing element therein so as to break away particles that contact a sensor surface. To achieve a high frequency oscillatory cycle, the sensing element is mounted to a cantilever vane capable of producing short rapid oscillations that produce shockwaves to dislodge particulates and water droplets from the sensor surface, leaving it clean to maintain reliable, accurate and repeatable sensing levels within calibrated response limits. Moreover, the oscillations can be utilized in a cleaning cycle to dry and/or remove contaminants from the sensor assemblies, for example post therapy session in an idle mode. Mechanical shockwave energy induced onto the sensor surface through oscillatory motion transforms rapidly reversing potential energy into kinetic energy creating moment of inertia to break away particulates before they become a permanent adhesion on a surface of the sensor assemblies 40, 42, and 46.

Figure 2:
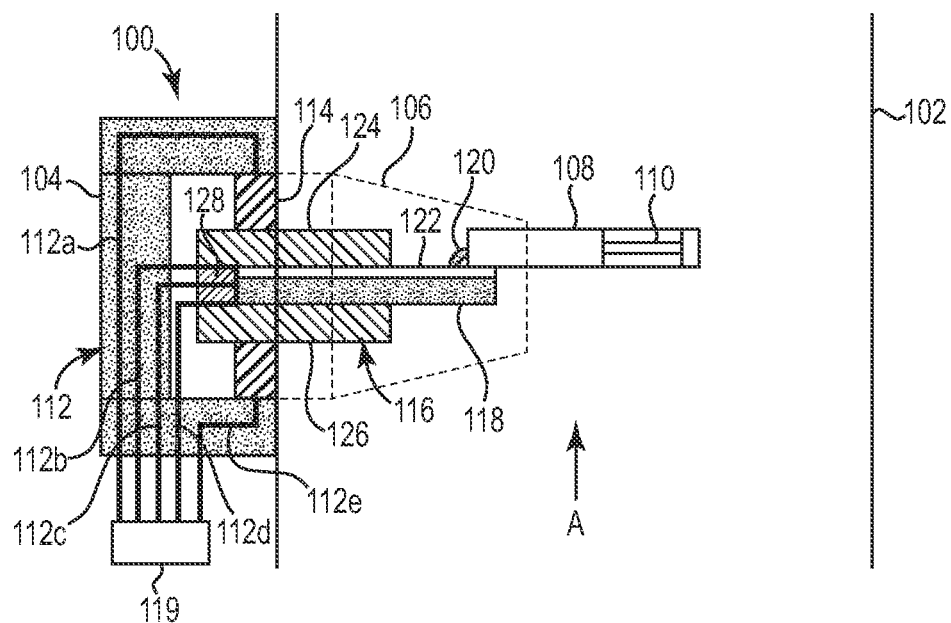
FIG. 2 is a schematic diagram of a sensor assembly positioned within a patient airway.

FIG. 2 is a schematic, sectional view of a sensor assembly 100 positioned within an airway 102 configured to actuate for reduction of contamination build-up thereon. Sensor assembly 100 can be used in FIG. 1 as one or more of sensor assemblies 40, 42 and 46, wherein airway 102 can be inspiratory tube 22, Y-connector 24 and/or expiratory tube 26. Sensor assembly 100 includes an assembly housing 104, a flexible seal 106 coupled to the assembly housing 104 and a sensing element housing 108 maintaining a sensing element 110. Assembly housing 104 is positioned outside the airway 102, whereas seal 106, sensing element housing 108 and sensing element 110 are positioned within the airway 102 to receive airflow, indicated by arrow 'A'.

Assembly housing 104 maintains a plurality of electrical connectors 112 (including connectors 112a-e) and a mounting element comprising a beam 114 configured to couple an actuator 116 (e.g., a piezoelectric actuator) and a printed circuit board (PCB) 118 to assembly housing 104. Connectors 112 are electrically coupled to a controller 119 that is configured to provide signals to and/or from the connectors 112. In one embodiment, controller 119 is part of humidifier 14, electrically coupled to connectors 112 through a cable (e.g., electrical connectors 38 and 44). Seal 106, in one embodiment, is a duckbill-type seal (e.g., as used on a trocar) configured to seal the actuator 116 and PCB 118 as well as provide flexibility to deflect upon operation of actuator 116.

Sensing element 110 can be formed of a capacitive or resistive membrane to sense relative humidity of gas within airway 102 and may further include a thermal sensing element such as a resistive temperature detector (RTD) or thermistor. Suitable sensing elements can be obtained from vendors such as Honeywell and Sensirion. PCB 118 is coupled to sensing element housing 108 (e.g., through a mechanical bond) and is further electrically coupled to sensing element 110 through an electrical connector 120 (e.g., solder, pins). In one embodiment, PCB 118 also includes a liquid resistant coating 122 (e.g., formed of paralyne) to protect the PCB 118.

Connectors 112a and 112e are electrically coupled to actuator 116. As discussed below, connectors 112a and 112e provide drive signals to actuator 116, ultimately causing PCB 118, sensing element housing 108 and sensing element 110 to oscillate within airway 102. Connectors 112b, 112c and 112d are electrically coupled to PCB 118 and sensing element 110. Collectively, connectors 112b-d provide power to components on PCB 118 and sensing element 110. Moreover, connectors 112b-d provide signals (e.g, to controller 119) indicative of measurements made by sensing element 110. Thus, sensor assembly 100 includes at least a first connector (e.g., connectors 112b-d) electrically coupled to sensing element 110 and at least a second connector (e.g., connectors 112a and 112e) electrically coupled to actuator 116. Controller 119 can include an oscillator to provide driving forces to actuator 116, for example a voltage to generate a force within actuator 116.

Actuator 116 is configured to oscillate sensing element housing 108 so as to prevent build up of contamination on the housing 108 and/or sensing element 110. In one embodiment, actuator 116 is an electro-mechanical transducer that possesses high motion and voltage sensitivity. As illustrated in FIG. 2, actuator 116 is a sandwich-like structure in which two thin piezoelectric ceramic elements 124 and 126 are bonded to a cantilevered center support vane 128 and positioned on the top and bottom of PCB 118. Vane 128 provides mechanical integrity and built-in leverage to amplify the motion and electrical output of the piezoelectric elements 124 and 126. In one embodiment, vane 128 forms a U-shaped channel so as to accommodate PCB 118 therein and surround PCB 118 on opposite sides. Vane 128 can be formed of various suitable materials such as brass, stainless steel, and/or an alloy, for example.

Elements 124 and 126 are electrically coupled to electrical connectors 112a and 112e, respectively. When an electric drive signal is applied via connectors 112a and 112e to elements 124 and 126, one ceramic element (e.g., element 124) expands laterally and the other element (e.g., element 126) contracts laterally. This opposing strain results in a bending or deflection of actuator 116 (thus providing deflection of sensing element 110) that is proportional to the voltage applied using electrical connectors 112a and 112e. Actuator 116 can generate large displacements and moderate forces at low levels of electrical drive. The resonant frequency to drive the actuator 116 is proportional to the dimensional characteristics of the piezoelectric elements 124 and 126 and serves to provide mechanical movement to PCB 118, sensing element housing 108 and sensing element 110.

As discussed above, particulate contamination can cause sensor failures and performance degradation. By employing actuator 116 to eliminate particle accumulation on sensing element 110, particulate contamination can be reduced. In particular, the sensor assembly 100 can be subject to high frequency oscillations introduced through actuator 116 that creates a continuous reversing potential energy, inducing an accelerated moment of inertia and kinetic energy within the particulates, thus breaking away their adhesion from the sensing element 110. Thus, the sensor assembly 100 is left clean and clearly exposed for repeatability and accuracy of sensing desired parameters.

Although the present disclosure has been described with reference to preferred embodiments, workers skilled in the art will recognize that changes can be made in form and detail without departing from the spirit and scope of the present disclosure.

What is claimed is:

1. A sensor assembly for positioning in a breathing tube of a patient circuit, comprising:
    a sensing element configured to measure a parameter associated with gas within the breathing tube, wherein the sensing element includes one of a resistive or a capacitive sensing element for sensing a relative humidity of the gas;
    an actuator comprising two layers with a vane positioned there-between, wherein the vane and a printed circuit board coupled to the vane are mechanically coupled to the sensing element such that the sensing element is positioned to protrude into an airway path within the breathing tube of the patient circuit;
    a first connector electrically coupled to the sensing element and configured to provide a measurement signal indicative of the measured parameter; and
    a second connector electrically coupled to the actuator and configured to provide a drive signal to the actuator to actuate the sensing element.

2. The sensor assembly of claim 1, wherein the parameter is associated with the relative humidity of the gas, and the sensing element is further configured to measure a further parameter, the further parameter associated with a temperature within the breathing tube.

3. The sensor assembly of claim 1, wherein the sensing element is maintained in a sensing element housing.

4. The sensor assembly of claim 1, wherein the two layers of the actuator are formed of a piezoelectric material.

5. The sensor assembly of claim 1, wherein the two layers are mechanically coupled to the sensing element via at least the vane.

6. The sensor assembly of claim 5, wherein a first layer of the two layers is above a first surface of the vane and a second layer of the two layers is below the first surface of the vane.

7. The sensor assembly of claim 1, wherein the drive signal is configured to drive the actuator at a resonant frequency.

8. The sensor assembly of claim 1, and further comprising:
    a seal positioned in the breathing tube and enclosing the actuator.

9. The sensor assembly of claim 1, wherein
    the printed circuit board is electrically coupled to the sensing element and the first connector.

10. The sensor assembly of claim 1, and further comprising:
    an assembly housing positioned outside the breathing tube and maintaining the first and second connectors.

11. A respiratory therapy system, comprising:
    a tube having an airway for transmitting gas; and
    a sensor assembly coupled to the airway, comprising:
        a sensing element configured to measure a parameter associated with gas within the airway, wherein the sensing element includes one of a resistive or a capacitive sensing element for sensing a relative humidity of the gas;
        an actuator comprising piezoelectric materials that are separated by a vane and a printed circuit board that are mechanically coupled to the sensing element such that the sensing element is positioned to protrude into an airway path within the airway of the tube;
        a first connector electrically coupled to the sensing element and configured to provide a measurement signal indicative of the measured parameter; and
        a second connector electrically coupled to the actuator and configured to provide a drive signal to the actuator to actuate the sensing element.

12. The respiratory therapy system of claim 11, wherein the parameter is associated with the relative humidity of the gas, and the sensing element is further configured to measure a further parameter, the further parameter associated with a temperature within the airway.

13. The respiratory therapy system of claim 11, wherein the sensing element is maintained in a sensing element housing.

14. The respiratory therapy system of claim 11, wherein the piezoelectric materials comprise two piezoelectric layers.

15. The respiratory therapy system of claim 14, wherein the drive signal causes a first piezoelectric layer of the two piezoelectric layers to expand laterally while a second piezoelectric layer of the two piezoelectric layers contracts laterally.

16. The respiratory therapy system of claim 15, wherein the vane is positioned between the two piezoelectric layers, the first piezoelectric layer of the two piezoelectric layers being above a first side of the vane and the second piezoelectric layer of the two piezoelectric layers being below the first side of the vane.

17. The respiratory therapy system of claim 11, wherein the drive signal is configured to drive the actuator at a resonant frequency.

18. The respiratory therapy system of claim 11, and further comprising:
    a seal positioned in the airway of the tube and enclosing the actuator.

19. The respiratory therapy system of claim 11, and further comprising:
    a printed circuit board electrically coupling the sensing element and the first connectors.

20. The respiratory therapy system of claim 11, and further comprising:
an assembly housing maintaining the first and second connectors.

21. A method of providing improved accuracy, reliability and/or repeatability of dosage for a respiratory therapy session, comprising:
positioning a sensing element to protrude into an airway path within an airway of a breathing tube, wherein the sensing element includes one of a resistive or a capacitive sensing element for sensing a relative humidity of gas;
using the sensing element, measuring a parameter associated with gas within the airway of the breathing tube;
coupling a proximal end of the sensing element to an actuator comprising a first layer and a second layer in a cantilevered fashion such that the proximal end of the sensing element is disposed between the first layer and the second layer, wherein a distal end of the sensing element is positioned within the airway of the breathing tube; and
providing a drive signal to the actuator to actuate the sensing element in order to reduce contamination on the sensing element.

22. The method of claim 21, wherein the parameter is associated with the relative humidity of the gas, and the sensing element is further configured to measure a further parameter, the further parameter associated with a temperature within the airway.

23. The method of claim 21, wherein the sensing element is maintained in sensing element housing.

24. The method of claim 21, wherein the actuator is formed of a piezoelectric material.

25. The method of claim 21, wherein the first layer and the second layer are formed of piezoelectric layers.

26. The method of claim 25, wherein the actuator is coupled to the sensing element through a vane that is positioned between the first and second piezoelectric layers such that the first piezoelectric layer is above a first side of the vane and a first side of the proximal end of the sensing element and the second piezoelectric layer is below the first side of the vane and the first side of the proximal end of the sensing element.

27. The method of claim 21, wherein the drive signal is configured to drive the actuator at a resonant frequency.

28. The method of claim 21, and further comprising:
providing a seal positioned in the airway of the breathing tube and enclosing the actuator.

* * * * *